(12) United States Patent
Murase et al.

(10) Patent No.: US 6,606,900 B2
(45) Date of Patent: Aug. 19, 2003

(54) GAS SENSOR HAVING PROTECTOR AND PROTECTION CAP

(75) Inventors: Masaaki Murase, Aichi (JP); Nobuo Kawai, Gifu (JP); Hiroshi Miyata, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/745,804

(22) Filed: Dec. 26, 2000

(65) Prior Publication Data

US 2002/0020210 A1 Feb. 21, 2002

(30) Foreign Application Priority Data

Dec. 27, 1999 (JP) .......................................... 11-369045

(51) Int. Cl.⁷ .................................................. G01N 7/00
(52) U.S. Cl. ..................... 73/31.06; 73/31.05; 73/23.21
(58) Field of Search .......................... 73/31.05, 31.06, 73/23.21, 23.32; 204/424–429

(56) References Cited

U.S. PATENT DOCUMENTS 4,597,850 A * 7/1986 Takahasi et al. ............ 204/426
6,222,372 B1 * 4/2001 Fukaya et al. .............. 204/424
6,279,376 B1 * 8/2001 Yamada et al. ............. 73/23.2

FOREIGN PATENT DOCUMENTS

| DE | 298 03 046 | 8/1999 |
| JP | 58-79148 | 5/1983 |
| JP | 9-184822 | 7/1997 |
| JP | 11-295263 | 10/1999 |

* cited by examiner

Primary Examiner—Robert Raevis
Assistant Examiner—Michael Cygan
(74) Attorney, Agent, or Firm—Sughrue Mion, PLLC

(57) ABSTRACT

A gas sensor including an element 4 for measuring the concentration of a gas to be detected which is contained in a gas under measurement; a protector 2 provided to cover a tip end of the element 4 in the axial direction; and a protection cap 1 removably attached to the gas sensor. The protection cap 1 includes a tubular portion 106 which surrounds a side surface 202 of the protector 2, support portions 102 which project from an inner surface 161 of the tubular portion 106 and reach the side surface 202 of the protector 2 without axially partitioning the space between the inner surface 161 of the tubular portion 106 and the side surface 202 of the protector 2, and an air-outlet hole 103 for establishing communication between the interior and exterior of the protection cap 1.

4 Claims, 6 Drawing Sheets

GAS SENSOR HAVING PROTECTOR AND PROTECTION CAP

BACKGROUND OF THE INVENTION

1. Field of the Invention

The present invention relates to a gas sensor for measuring the concentration of a gas to be detected, which is contained in a gas under measurement, such as exhaust gas discharged from an internal combustion engine or the like.

2. Description of the Related Art

Conventionally, an oxygen sensor having a tubular element as described in Japanese Patent Application Laid-open Nos. 9-184822 and 11-295263 has been known and used as a gas sensor for measuring the concentration of a gas to be detected which is contained in a gas under measurement. Further, an oxygen sensor described in German Utility Model Publication No. 29803046 is provided with a protection cap for transportation. When the oxygen sensor is transported, the protection cap is attached to the oxygen sensor.

3. Problems Solved by the Invention

In the above-described conventional gas sensor, an element 4 for detecting a gas is inserted into and accommodated within a metallic shell 3; and in order to protect the element 4, a protector 2 is provided at the axial tip end of the gas sensor so as to cover the element 4. When the gas sensor is transported, a protection cap 1 made of resin is provided around the protector 2 to thereby protect the element 4. The protection cap 1 prevents splashing of water on the element 4 and prevents the element 4 from coming in contact with outside air during transportation and causing deterioration in properties. An annular projection 101 is provided on the inner surface of the protection cap 1 in order to prevent, to the extent possible, contact between outside air and the element 4. Further, in order to prevent contact between outside air and the element 4 via communication holes 201, which are provided to allow a detection gas to contact the element 4 during use of the gas sensor, the space around the communication holes 201 is hermetically sealed.

However, since a seizure-prevention agent 303 (NEVER SEEZE: Product of BOSTIC, etc.) is applied to a male-screw portion of the gas sensor in order to prevent seizure of the male-screw portion, which would otherwise occur upon attachment to an exhaust pipe, when the protection cap 1 is attached to the gas sensor, a solvent contained in the seizure-prevention agent 303 evaporates and fills the interior of the protection cap 1, thereby adversary affecting the characteristics of the element. This is because even when the solvent fills the interior of the protection cap 1, the solvent is not replaced with outside air due to presence of the protection cap 1.

Further, since an airtight seal must be provided between the protection cap 1 and the protector 2, the inner diameter of the projection must be changed in accordance with the size of the protector 2. Therefore, various types of protection caps 1 must be prepared and used selectively in accordance with the type of a sensor to be protected.

SUMMARY OF THE INVENTION

The present invention has been accomplished in order to solve the above-described problems. It is therefore an object of the present invention to prevent the element characteristics of a gas sensor from being deteriorated by a solvent evaporated from the seizure-prevention agent 303, which deterioration would otherwise occur when the protection cap 1 is attached to the gas sensor before transportation thereof, thus causing the interior of the protection cap 1 to be filled with the evaporated solvent.

In order to achieve the above-described object, the present inventor employed the following configuration. Each of support portions 102—which are adapted to come into elastic contact with a protector side surface 202 to thereby support a protection cap 1 relative to the protector 2—projects from a tubular-portion inner surface 161 of the protection cap 1 in such a manner that the space between the protector 2 and the tubular portion 106 of the protection cap 1 attached around the protector 2 is not partitioned axially; and an air-outlet hole 103 is formed in the protection cap 1 in order to release a solvent evaporated from a seizure-prevention agent 303. This structure prevents the solvent evaporated from the seizure-prevention agent 303 from filling the interior of the protection cap 1, to thereby prevent the solvent from adversely affecting the element characteristics.

Since the protection cap 1 of the present invention is designed such that gas in the vicinity of the element is replaced with outside air, the element is affected slightly by the outside air. However, since the tubular portion 106 of the protection cap 1 is formed to cover the protector 2, direct contact with water can be prevented to some degree.

Each of the support portions 102 may assume a shape of a plate that extends radially from the tubular-portion inner surface 161 toward the center axis of the sensor and reaches the protector side surface 202. This plate-shaped configuration enables a greater portion of the area between the protection cap 1 and the protector 2 to be maintained unclosed. Thus, the ventilation efficiency is improved further. Further, when the protection cap 1 is formed of a soft resin, the protection cap 1 can be used for a different gas sensor whose protector 2 has a larger diameter, because the plate-shaped support portions 102 projecting from the tubular-portion inner surface 161 easily deform, as shown in FIG. 3. The material of the protection cap is not limited to resin, and may be composed, for example, of paper. Further, a resin having elasticity such as rubber is preferred because use of such an elastic resin facilitates the work of attaching the protection cap to the gas sensor and prevents the protection cap from accidentally coming off the gas sensor.

The air-outlet hole 103 is preferably provided at the tip end of the protection cap 1. In this case, water does not splash onto the element even when communication holes 201 are formed on the protector side surface 202. When a communication hole 201 is formed at the tip end surface of the protector 2, the air-outlet hole 103 is preferably formed at the tubular portion 106 of the protection cap 1, as shown in FIG. 6. However, when the communication hole 201 is small, the air-outlet hole 103 may be provided on the tip end surface of the protection cap 1. At first glance, provision of the communication hole 201 in the vicinity of a region at which the seizure-prevention agent 303 is applied seems to provide good air ventilation. However, in this case, air in the vicinity of the element may not be replaced with outside air. In order to solve this problem, the air-outlet hole 103 of the protection cap 1 is provided in the vicinity of the communication hole 201 of the protector 2 in order to promote replacement of air in the vicinity of the element with outside air. The communication hole 201 of the protector 2 and the air-outlet hole 103 of the protection cap 1 are preferably arranged such that the element 4 is not present on a straight line passing through both holes, because this arrangement prevents splashing of water onto the element 4.

DESCRIPTION OF REFERENCE NUMERALS

Figure 1:
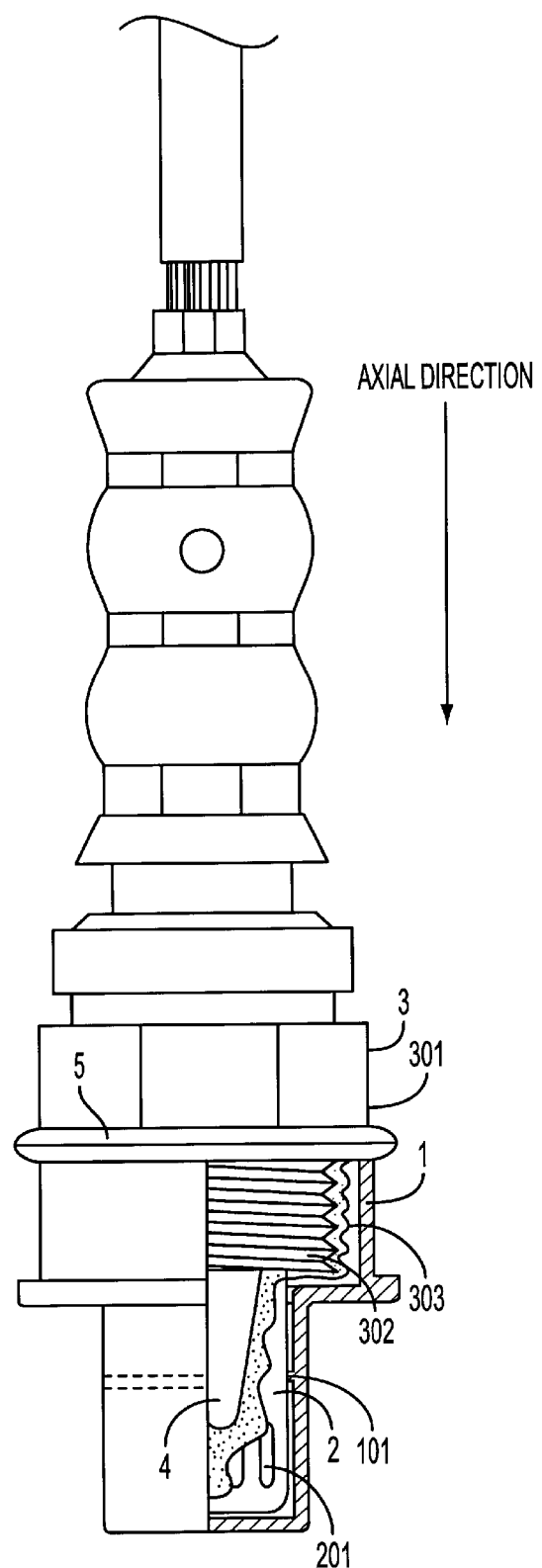
FIG. 1 shows a gas sensor and a conventional protection cap attached thereto.

1 . . . protection cap
2 . . . protector
3 . . . metallic shell
4 . . . element
5 . . . metal packing
102 . . . support portions
103 . . . air-outlet hole
104 . . . skirt portion
105 . . . flange portion
106 . . . tubular portion

DESCRIPTION OF THE PREFERRED EMBODIMENTS

Next, embodiments of the present invention will be described by way of example, however, the present invention should not be construed as being limited thereto.

Figure 2A:
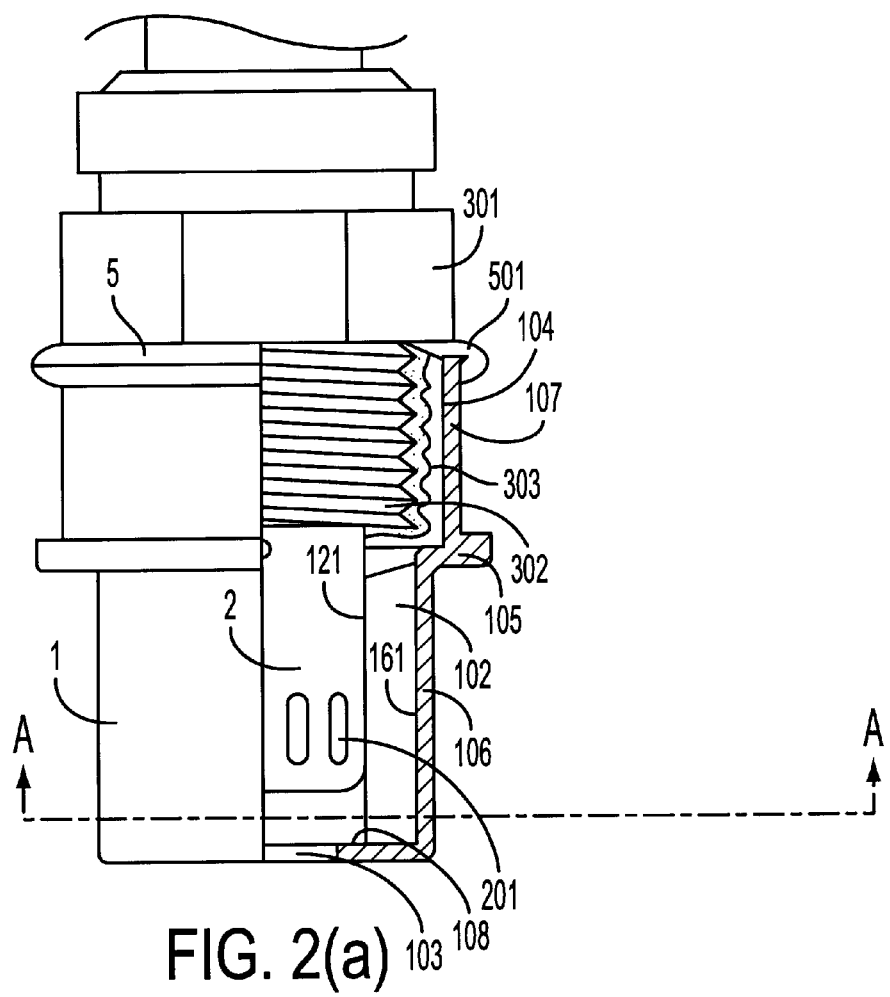
FIG. 2(a) shows a gas sensor and FIG. 2(b) shows a protection cap of the present invention (tip end portion only) attached thereto.
Figure 2B:
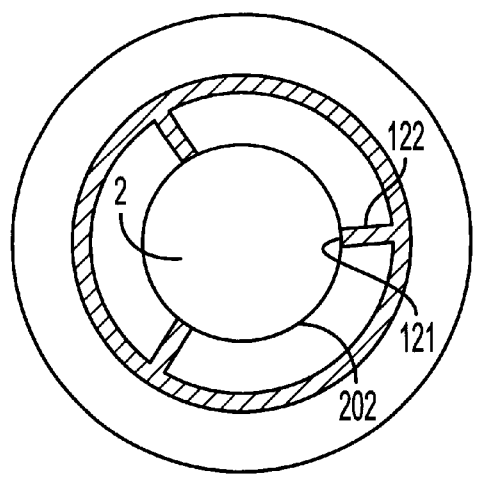

FIG. 2 shows a tip end portion of a gas sensor for measuring the concentration of oxygen in a gas under measurement with a protection cap 1 attached to the gas sensor. The metallic shell has a hexagonal portion 301 at its axial center and a male screw portion 302 of M18 formed on the tip-end side of the hexagonal portion 301. The hexagonal portion 301 has an axial length of 5 mm and a diametric dimension of 22 mm as measured between opposite sides. A protector 2 assuming the shape of a cup having a closed end is joined by spot welding to the distal end of the male screw portion 302 so as to cover an element 4. Communication holes 201 are formed in a distal end portion of a protector side surface 202 in order to permit a detection gas to flow toward the element 4. A seizure-prevention agent 303 such as NEVER SEEZE (product of BOSTIC) is applied to the surface of the male-screw portion 302. Further, a metal packing 5 is fitted to the base end portion of the male screw portion 302 in order to provide sealing between the gas sensor and an exhaust pipe to which the gas sensor is attached, to thereby prevent leakage of exhaust gas.

A protection cap 1 made of polyethylene is attached to the gas sensor to surround the protector 2. The protection cap 1 has a tubular portion 106 for protecting the element 4 from, for example, splashed water. The protection cap 1 has a flange portion 105 projecting from the base end of the tubular portion 106. The flange portion 105 facilitates the work of attaching the protection cap 1 to the gas sensor and removing the same from the protection cap 1. A skirt portion 104 is further formed to extend from the flange portion 105 toward the base end of the protection cap 1, and an end portion 107 of the skirt portion 104 located on the base-end side is designed to have a size that enables fitting of that end portion into a concave portion 501 of the metal packing 5. The skirt portion 104 prevents the seizure-prevention agent 303 on the male screw portion 302 from dirtying clothes or hands of a worker while transporting the gas sensor and also prevents the gas sensor from being fixed to the exhaust pipe due to seizure, which would otherwise occur due to loss of the seizure-prevention agent 303. Further, since the skirt portion 104 is fitted into the concave portion 501 of the metal packing 5, even when a lateral force acts on the skirt portion 104, the skirt portion 104 hardly moves. Therefore, adhesion of the seizure-prevention agent 303 onto the inner surface of the skirt portion 104 can be prevented.

An air-outlet hole 103 is formed at the tip end of the protection cap 1 in order to prevent vapor of a solvent contained in the seizure-prevention agent 303 from filling the interior of the protection cap 1. When the air-outlet hole 103 is excessively large, the problem of water splashing on the element 4 occurs. When the air-outlet hole 103 is excessively small, solvent vapor is not released. Therefore, the air-outlet hole 103 is formed to have an appropriate size. In the present embodiment, a hole having a diameter of 6 mm is formed. Further, some clearance is desirably provided between the tip end surface of the protector 2 and the inner surface 108 of the distal end portion of the protection cap 1 in which the air-outlet hole 103 is formed. When the clearance is excessively small, flow of air toward the air-outlet hole 103 is hindered, and the function of protecting the element 4 from water deteriorates. However, when the clearance is excessively large, handling of the gas sensor during, for example, transport thereof becomes difficult, and the protection cap 1 becomes likely to come off. Therefore, the clearance is set to an appropriate size. In the present embodiment, the clearance is set to 5 mm.

Figure 3:
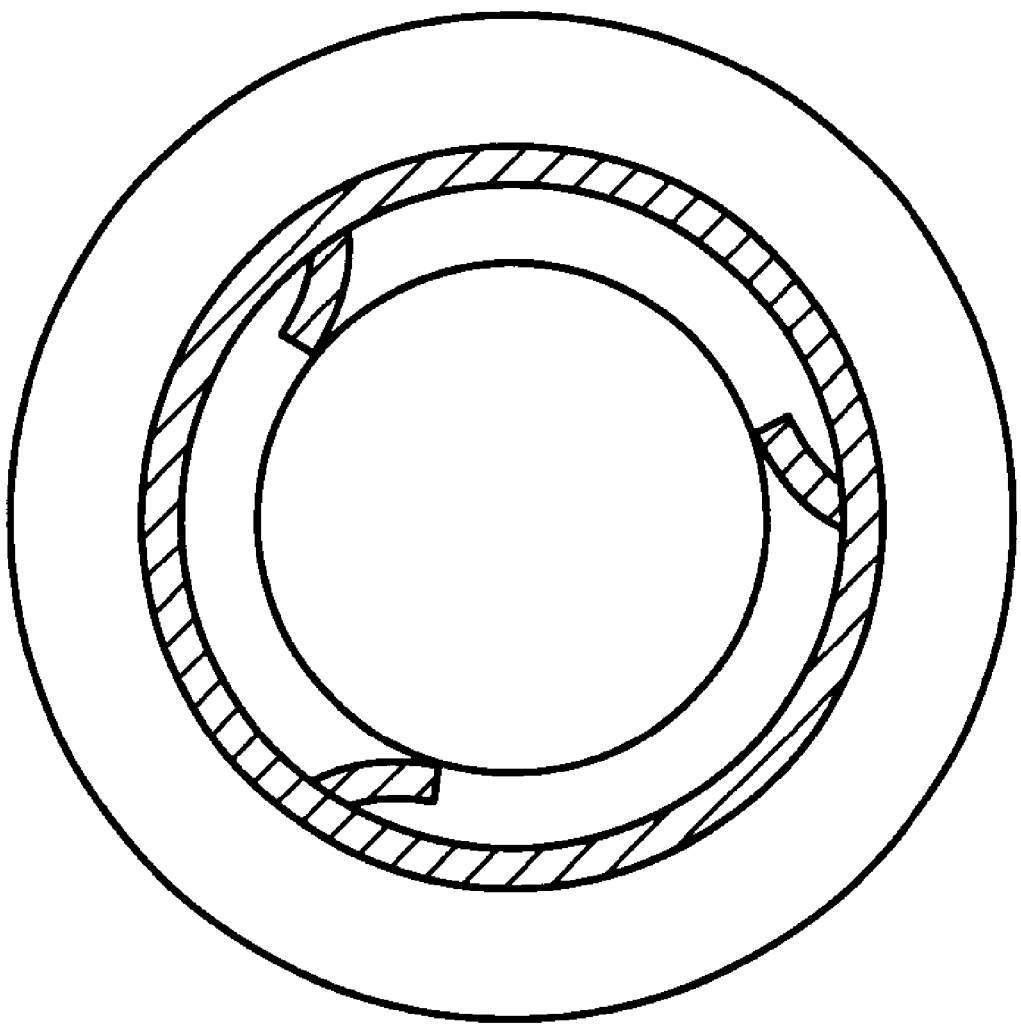
FIG. 3 is a sectional view of a tip end portion of a gas sensor whose protector has a larger diameter and a protection cap of the present invention attached thereto.

Support portions 102 each having a plate-like shape project from the tubular-portion inner surface 161 of the protection cap 1 in order to enable attachment of the protection cap 1 to the gas sensor. Lateral side surfaces 121 of the support portions 102 come into elastic contact with a protector side surface 202, so that the protection cap 1 is supported by the protector 2. Since the support portions 102 are formed such that their plate surfaces 122 are parallel to the axis of the gas sensor, a large amount of air can pass through the space between the protector 2 and the tubular portion 106. Therefore, effective ventilation of air from the region where the seizure-prevention agent 303 is present to the air-outlet hole 103 becomes possible, whereby influence of the solvent on the element 4 can be reduced. Three support portions 102 are disposed at equal angular intervals (120 degrees) in the circumferential direction. The number of the support portions 102 may be two. However, provision of three or more support portions 102 is desired, because the protection cap 1 can be supported by the protector 2 more stably. However, provision of an excessively large number of support portions 102 makes attachment of the protection cap 1 difficult, and therefore is not preferred. An excessively large thickness of the support portions 102 also makes attachment of the protection cap 1 difficult, and therefore is not preferred. In the present embodiment, the thickness of the support portions 102 is set to 0.5 mm. This thickness allows the support portions 102 to deform easily. Therefore, when the protection cap 1 is attached to a gas sensor whose protector 2 has a larger diameter, the support portions 102 deform as shown in FIG. 3, enabling the protection cap 1 to be attached to the gas sensor without difficulty.

Figure 4A:
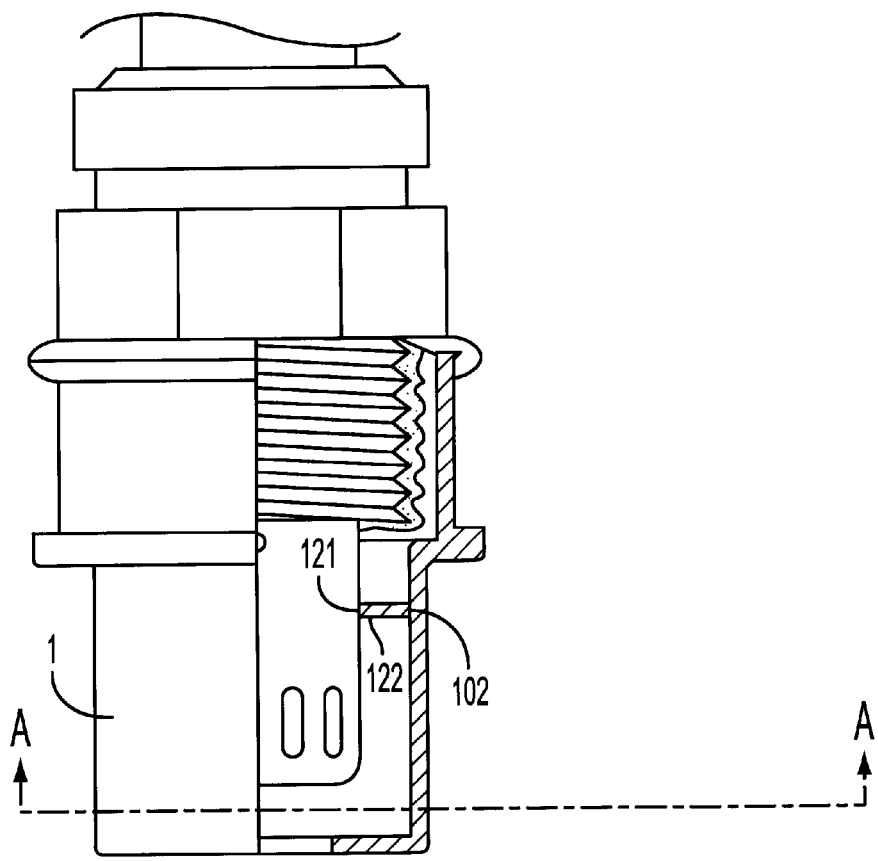
FIG. 4(a) shows a gas sensor and FIG. 4(b) shows a modified protection cap according to the present invention.
Figure 4B:
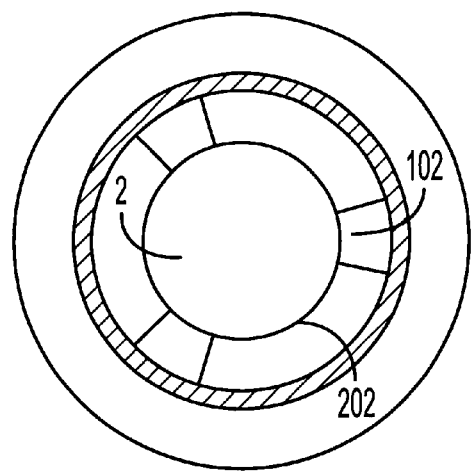
Figure 5A:
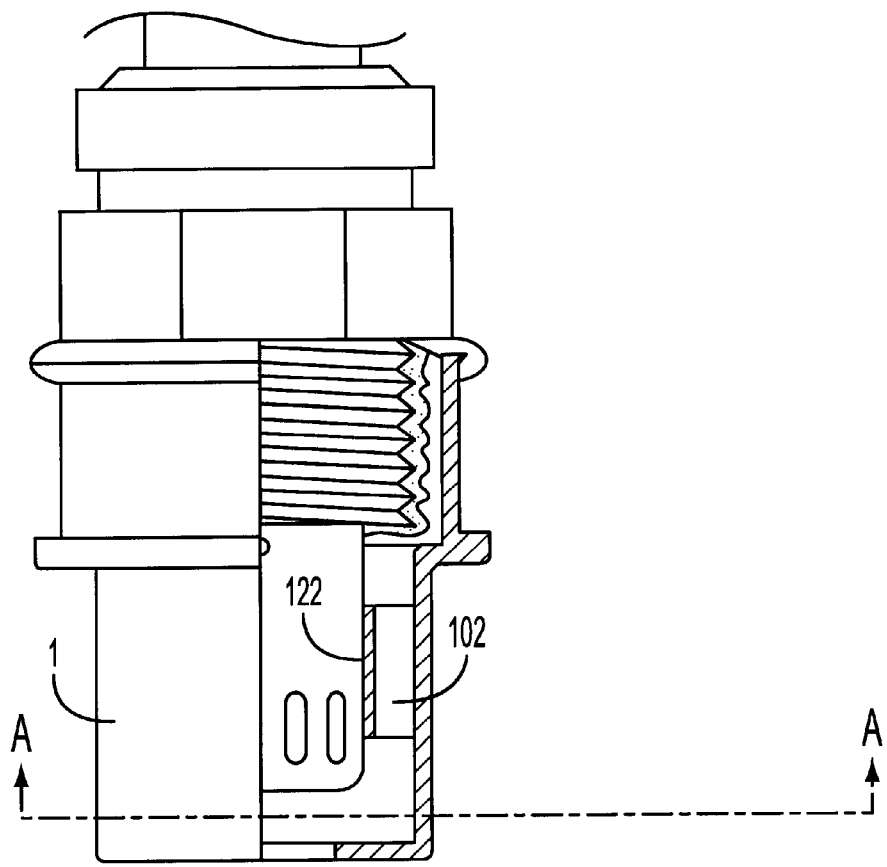
FIG. 5(a) shows a gas sensor and FIG. 5(b) shows another modification of the protection cap according to the resent invention.
Figure 5B:
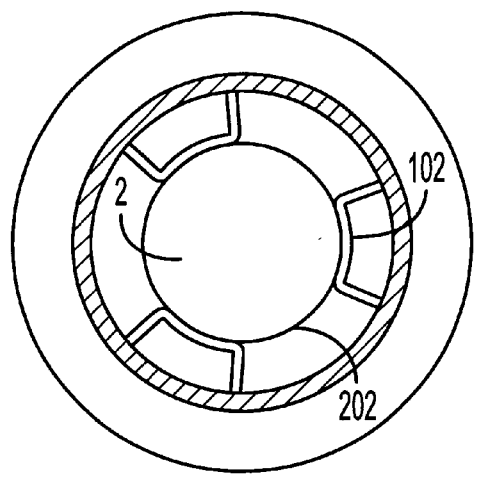

As shown in FIG. 4, the support portions 102 may be provided such that their plate surfaces extend perpendicular to the center axis of the gas sensor. Alternatively, as shown in FIG. 5, the opposite lateral end surfaces of each support portion 102 are jointed to the tubular portion 106 such that the plate face of the support portion 102 comes into elastic contact with the protector 2 to thereby support the same.

Figure 6A:
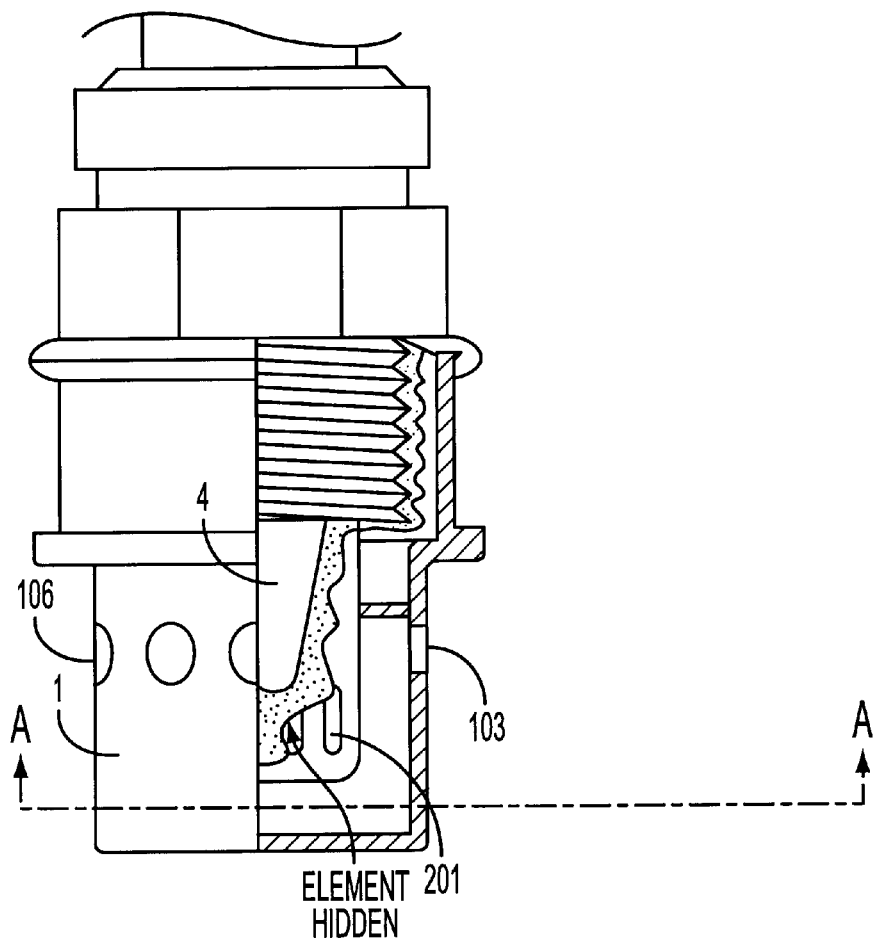
FIG. 6(a) shows a gas sensor and FIG. 6(b) shows another modification of the protection cap according to the present invention.
Figure 6B:
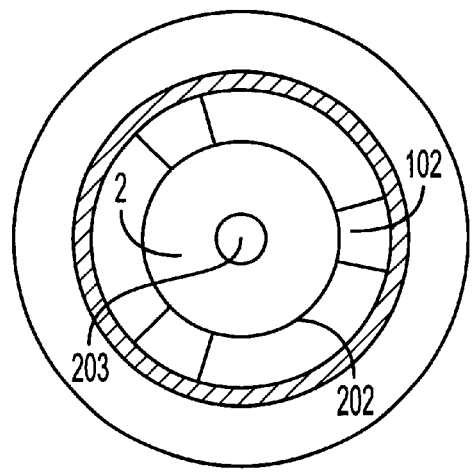

The position of the air-outlet hole 103 is not limited to the tip end surface of the protection cap 1. As shown in FIG. 6, the air-outlet hole 103 may be provided in the circumferential wall of the tubular portion 106 of the protection cap 1. This configuration is preferable in a particular case in which a communication hole 203 is formed on the tip end surface of the protector 2 as shown in FIG. 6, because the provision of the air-outlet hole 103 in the circumferential wall of the tubular portion 106 can prevent water from splashing on the element. When communication holes 201 are also formed on the protector side surface 202, the air-outlet hole 103 is desirably provided in the circumferential wall of the tubular portion 106 such that the element 4 is not present on a straight line passing through both holes, because this arrangement more effectively prevents water splashing.

It should further be apparent to those skilled in the art that various changes in form and detail of the invention as shown and described above may be made. It is intended that such changes be included within the spirit and scope of the claims appended hereto.

This application is based on Japanese Patent Application No. Hei. 11-369045, filed Dec. 27, 1999, which is incorporated herein by reference in its entirety.

What is claimed is:

1. A gas sensor comprising:

an element for measuring the concentration of a gas to be detected which is contained in a gas under measurement;

a protector covering a tip end of the element in the axial direction; and a protection cap removably attached to the gas sensor, which comprises a tubular portion surrounding a side surface of the protector, support portions which project from an inner surface of the tubular portion and reach the side surface of the protector without axially partitioning the space between the inner surface of the tubular portion and the side surface of the protector, and an air-outlet hole for establishing communication between the interior and exterior of the protection cap, wherein a plate surface of the support portions extends parallel to the axial direction.

2. The gas sensor as claimed claim 1, wherein the support portions assume a plate-like shape.

3. The gas sensor as claimed in claim 2, wherein a lateral side surface of the support portions is in contact with the protector side surface.

4. The gas sensor as claimed in claim 1, wherein the air-outlet hole is formed at the tip end of the protection cap.

* * * * *